United States Patent
Majercak (10) Patent No.: US 10,130,384 B2
(45) Date of Patent: Nov. 20, 2018

(54) CATHETER SYSTEMS AND METHODS FOR RE-ENTRY IN BODY VESSELS WITH CHRONIC TOTAL OCCLUSION

(71) Applicant: Cordis Corporation, Fremont, CA (US)

(72) Inventor: David Majercak, Livermore, CA (US)

(73) Assignee: CARDINAL HEALTH SWITZERLAND 515 GMBH, Bar Zug (CH)

( * ) Notice: Subject to any disclaimer, the term of this patent is extended or adjusted under 35 U.S.C. 154(b) by 439 days.

(21) Appl. No.: 14/493,711

(22) Filed: Sep. 23, 2014

(65) Prior Publication Data

US 2016/0081709 A1    Mar. 24, 2016

(51) Int. Cl.

| | |
|---|---|
| A61B 17/3207 | (2006.01) |
| A61M 25/10 | (2013.01) |
| A61M 25/04 | (2006.01) |
| A61B 17/00 | (2006.01) |
| A61B 17/22 | (2006.01) |
| A61M 25/00 | (2006.01) |
| A61M 25/01 | (2006.01) |

(52) U.S. Cl.
CPC ..... *A61B 17/3207* (2013.01); *A61M 25/0194* (2013.01); *A61M 25/04* (2013.01); *A61M 25/104* (2013.01); *A61B 2017/00331* (2013.01); *A61B 2017/22002* (2013.01); *A61B 2017/22061* (2013.01); *A61B 2017/22071* (2013.01); *A61B 2017/22095* (2013.01); *A61M 2025/0095* (2013.01); *A61M 2025/0096* (2013.01); *A61M 2025/018* (2013.01); *A61M 2025/0197* (2013.01); *A61M 2025/1047* (2013.01)

(58) Field of Classification Search
CPC ..... A61B 17/3207; A61B 2017/22095; A61M 2025/0197; A61M 2025/0095; A61M 25/04; A61M 25/0194
See application file for complete search history.

(56) References Cited

U.S. PATENT DOCUMENTS

| | | | |
|---|---|---|---|
| 5,409,469 A * | 4/1995 | Schaerf | A61M 25/0662 604/160 |
| 6,231,546 B1 | 5/2001 | Milo | |
| 8,075,580 B2 | 12/2011 | Makower | |
| 2002/0107478 A1* | 8/2002 | Wendlandt | A61B 1/00156 604/95.01 |
| 2005/0171478 A1* | 8/2005 | Selmon | A61B 17/3207 604/164.01 |

(Continued)

FOREIGN PATENT DOCUMENTS

| | | |
|---|---|---|
| WO | 9949926 A2 | 10/1999 |
| WO | 2009076224 A1 | 6/2009 |

OTHER PUBLICATIONS

International Search Report and Written Opinion for PCT Application No. PCT/US2015/051452, dated Feb. 2, 2016.

(Continued)

*Primary Examiner* — Thomas McEvoy (74) *Attorney, Agent, or Firm* — Nada J. Ardeleanu (57) ABSTRACT

A catheter system and corresponding methods are provided for accessing a blood vessel true lumen from a sub-intimal plane of the vessel. The catheter includes components that are symmetric about the longitudinal axis and allow for reentry without the need to ensure a correct orientation of the cannula.

6 Claims, 8 Drawing Sheets

(56) References Cited

U.S. PATENT DOCUMENTS

| | | | |
|---|---|---|---|
| 2008/0243065 A1 | 10/2008 | Rottenberg et al. | |
| 2010/0145265 A1* | 6/2010 | Min | A61M 25/0084 |
| | | | 604/95.03 |
| 2013/0072957 A1 | 3/2013 | Anderson | |
| 2013/0317534 A1 | 11/2013 | Zhou et al. | |
| 2014/0200603 A1* | 7/2014 | Zhou | A61B 17/3207 |
| | | | 606/185 |
| 2014/0277053 A1* | 9/2014 | Wang | A61M 25/0194 |
| | | | 606/185 |

OTHER PUBLICATIONS

Office Action dated Feb. 7, 2018 for European Application No. EP15771490, pp. 1-5, filed Apr. 7, 2017.

\* cited by examiner

CATHETER SYSTEMS AND METHODS FOR RE-ENTRY IN BODY VESSELS WITH CHRONIC TOTAL OCCLUSION

BACKGROUND

An interventional guide wire or other interventional device is often used in medical procedures that attempt to establish a pathway through a heavily stenosed or chronically occluded vessel. A chronically occluded vessel is referred to as containing a chronic total occlusion CTO. During these procedures, the guide wire or device can only be of clinical benefit to establish vessel patency if it is advanced distally into the vessel true lumen.

At times during the process of advancing the guide wire or device through the stenosed vessel or CTO, and beyond the control of the operator, the guide wire or device may inadvertently enter into the wall of the vessel itself, i.e. the sub-intimal plane or space, or dissection plane. Once in this sub-intimal plane, it becomes difficult to navigate the guide wire or device through the sub-intimal tissue to re-gain access into the vessel true lumen at points distal to the occlusion, i.e., a "re-entry" into the vessel lumen from the sub-intimal space but around the CTO. The layer of tissue that separates the vessel true lumen from the sub-intimal plane is typically in the range from 100 to 500 micrometers for vessels in the diameter range from 2 mm to 4 mm, and from 100 to 3000 microns, in the largest vessels of the body.

There exist a variety of catheters for re-entry around a CTO. One is described and shown in U.S. Pat. No. 6,231,546. In the system of this US Patent, the re-entry catheter requires the operator to rotate a catheter shaft while observing a radiopaque marker on the catheter shaft to ensure that a side or lateral port is aimed at the true lumen of the blood vessel. Once the marker indicates the correct orientation of the lateral port, a cannula is extended through the lateral port in order to penetrate through the intimal layer of the blood vessel. It is believed that one drawback of this system is the requirement to rotate the catheter to the correct position while under fluoroscopic imaging otherwise an incorrect orientation of the cannula could cause internal hemorrhaging of the blood vessel.

Another system is described and illustrated in US Patent Application Publication 2013/0072957. In this publication, a balloon is used to orient the cannula into the proper orientation for re-entry into the true vessel lumen. To achieve this, the catheter utilizes an asymmetrical catheter lumen for the cannula. It is believed that this system also suffers from a similar drawback in that the lateral port of the cannula must be oriented in the correct direction towards the true lumen while under fluoroscopy. This is to ensure that the cannula does not penetrate away from the true lumen, which could lead to internal hemorrhaging.

SUMMARY OF THE DISCLOSURE

Recognizing these shortcomings of the aforementioned prior art, I have devised a heretofore new device that overcome these shortcomings. In particular, I have devised a catheter system that includes a catheter handle, a catheter body, a movable catheter sheath, an inner catheter shaft, a cannula, and a guidewire. The catheter handle extends along a longitudinal axis from a first end to a second end. The handle has a hollow tubular portion extending through the handle, a fitting proximate the first end, a hemostatic fitting proximate the second end and a side port disposed between the first and second ends. The catheter body extends from the catheter handle along the longitudinal axis from a proximal catheter end to a distal catheter end. The catheter body includes an articulation joint interposed between portions of the catheter body proximate the distal end. The movable catheter sheath has a portion surrounded by an internal surface of the catheter body and configured for movement along the longitudinal axis with respect to the catheter body. The catheter sheath extends through the catheter handle. The inner catheter shaft has a portion surrounded by an internal surface of the movable catheter sheath, the inner catheter shaft having an expandable frame attached proximate and end of the inner catheter shaft. The inner catheter shaft includes a terminal end proximate the distal end, where the terminal end has a plurality of slots extending along the longitudinal axis to allow the expandable arms to extend through respective slots. The cannula has a portion surrounded by an internal surface of the inner shaft and disposed for movement with respect to the inner shaft, and the cannula is configured to extend to the handle. The guidewire has a portion surrounded by an internal surface of the cannula, the guidewire configured to extend through the cannula to the handle.

In yet another variation, I have devised an endovascular catheter that includes a catheter body, inner catheter shaft and a cannula. The catheter body extends along the longitudinal axis from a proximal catheter end to a distal catheter end. The catheter body includes an articulation joint interposed between portions of the catheter body proximate the distal end. The inner catheter shaft has a portion surrounded by an internal surface of the catheter body. The inner catheter shaft has an expandable frame attached proximate and end of the inner catheter shaft. The inner catheter shaft includes a terminal end proximate the distal end, the terminal end having a plurality of slots extending along the longitudinal axis to allow arm portions of the expandable frame to extend through respective slots. The cannula has a portion surrounded by an internal surface of the inner shaft and disposed for movement with respect to the inner shaft, the cannula configured to extend through the inner catheter shaft.

In yet a further variation, I have devised an inner catheter shaft for use with a catheter that includes a body and an expandable frame. The body extends along a longitudinal axis from a first end to a second end with a plurality of openings extending through a conical surface of the second end to define generally elliptical through-slots into the conical surface. The expandable frame has a plurality of arms extending through respective through slots to connect to a hub portion proximate the second end. The body includes a cannula opening extending through the first end to the second end to allow insertion of a cannula.

In yet another embodiment, I have devised a technique for re-entry around a chronic total occlusion of a blood vessel with a specially configured catheter. The catheter includes a catheter body extending along the longitudinal axis from a proximal catheter end to a distal catheter end. The catheter body includes an articulation joint interposed between portions of the catheter body proximate the distal end, an inner catheter shaft having a portion surrounded by an internal surface of the catheter body, the inner catheter shaft having an expandable frame attached proximate and end of the inner catheter shaft, the inner catheter shaft including a terminal end proximate the distal end, the terminal end having a plurality of slots extending along the longitudinal axis to allow arm portions of the expandable frame to extend through respective slots and retained to the inner catheter shaft; and a cannula having a portion surrounded by an internal surface of the inner shaft and disposed for movement with respect to the inner shaft, the cannula configured to extend through the inner catheter shaft. The method can be achieved by: extending the catheter into a space between an intimal layer and an advential layer of the blood vessel before a chronic total occlusion; advancing the catheter until a terminal end of one of the cannula is past the chronic total occlusion; expanding the expandable frame against the intimal layer and the advential layer so that a bulge is formed by the intimal layer into the flow passage of the blood vessel; and advancing the cannula through the intimal layer into the flow passage of the blood vessel.

Alternative embodiments of the invention can be achieved when utilized with other features noted hereafter with the embodiments referenced earlier. For example, the catheter body may include a stiffened portion closer to the distal end than the proximal end, the stiffened portion having a higher Shore A Hardness than a Shore A Hardness of the catheter body; the expandable frame may include plurality of self-expanding arms disposed radially about the longitudinal axis; each of the self-expanding arms may include a free end; the self-expanding arms are joined together at opposite ends; the self-expanding arms comprise a nitinol material; a stiffened portion closer to the distal end than the proximal end, the stiffened portion having a higher Shore A Hardness than a Shore A Hardness of the catheter body; the expandable frame may include plurality of self-expanding arms disposed radially about the longitudinal axis; each of the self-expanding arms may include a free end; the self-expanding arms are joined together at opposite ends; the self-expanding arms comprise a nitinol material. The method may further include the following variations: moving one of the inner catheter shaft and catheter body with respect to the other to allow the expandable frame to expand against the intimal and advential layers; the catheter further may include a retractable sheath disposed between the catheter body and the inner catheter shaft; and the expanding step may include retracting the retractable sheath to expose the expandable frame so that the expand frame contacts the intimal and advential layers.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF DRAWINGS

The accompanying drawings, which are incorporated herein and constitute part of this specification, illustrate presently preferred embodiments of the invention, and, together with the general description given above and the detailed description given below, serve to explain features of the invention wherein like numerals represent like elements, in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the root terms "distal" or "proximal" are referenced in relation to a user in which "distal" indicates that certain parts or components are further away to the user and "proximal" indicates that certain parts or components are closer to the user. It is noted that the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

A catheter-based system, or catheter system, is described for the purpose of gaining access to the true lumen of a blood vessel coronary or peripheral artery or vein from a space within the vessel wall itself, referred to herein as a sub-intimal plane, or dissection plane. Throughout this document, the various catheter embodiments are referred to as the re-entry catheter or catheter system.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of the embodiments of the invention.

Figures 1, 2:
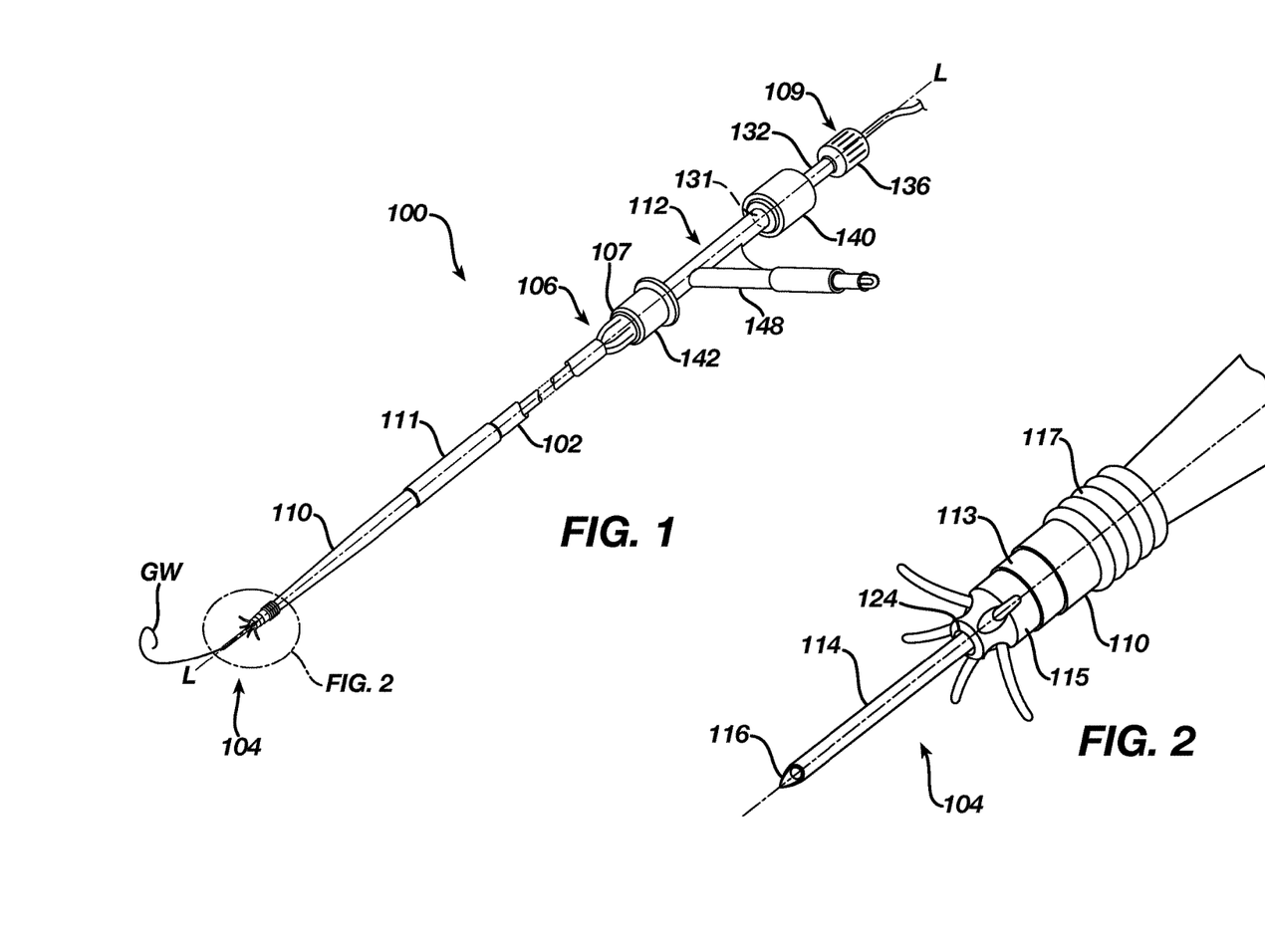
FIG. 1 illustrates a perspective view of one embodiment of the catheter system 100.
FIG. 2 illustrates a close up perspective view of the distal end of the system in FIG. 1.

Referring now to the figures wherein like numerals indicate the same element throughout the views, there is shown in FIG. 1 a catheter system 100. Catheter system 100 may include a catheter body 102 having a distal end 104 and a proximal end 106. Catheter body 102 includes a single lumen and a deflecting housing 110 secured to the distal end 104 thereof with a stiffer or stiffened section 111 interposed between the deflectable housing 110 and catheter handle 112. The catheter handle 112 is secured to the proximal end 106 of catheter body 102, and an axially translatable cannula is disposed within lumen 108. The cannula 114 has a sharpened tip 116, typically formed from a metal, hard plastic, composite, or the like, optically being radiopaque. Alternatively or additionally, it may be desirable to provide at least one separate radiopaque marker or the cannula at or near its distal end to facilitate visualization under fluoroscopic imaging. The deflector catheter housing 110 also includes a distal port 124 to permit introduction of the catheter 100 over the proximal end of a guidewire GW. The guidewire GW will pass through the distal port 124 and into the distal end 106 of the cannula 114 and travel through a lumen of cannula 114 all the way to the proximal end 106 of the catheter 100.

The catheter handle 112 extends along a longitudinal axis L-L from a first end 107 to a second end 109. The handle 112 has a hollow tubular portion 131 extending through the handle 112, a fitting 142 proximate the first end 107, a hemostatic fitting 140 proximate the second end 109 and a side port 148 disposed between the first and second ends 107, 109;

The catheter body 102 extends from the catheter handle 112 along the longitudinal axis L-L from a proximal catheter end 106 to a distal catheter end 104. In the enlarged view of the distal end 104 in FIG. 2, the distal end 104 includes an articulation joint 117 interposed between portions of the catheter housing 110 proximate the distal end 104. In one embodiment, the articulation joint 117 is disposed between the distal port 124 and the stiffened section 111 of the catheter housing 110. Although the articulation joint 117 is shown as a series of bellow-like members connected together to allow for a limited range of spherical movement, other articulation joint can be utilized, such as, for example, a spherical joint with stop members and the like.

The catheter body 102 is formed from a suitable biocompatible material, such as, for example, thermoplastic elastomer, i.e., polyether block amide (trade name PEBAX). Preferably, where utilized, the stiffened portion or section 111 is closer to the distal end than the proximal end and may have greater stiffness as quantifiable by a higher Shore D hardness value than the Shore D hardness of the remaining portion of the catheter body 102. Alternatively, the flexural modulus of the stiffened portion 111 should be higher than the remaining portion of the catheter body 102.

Figure 3A:
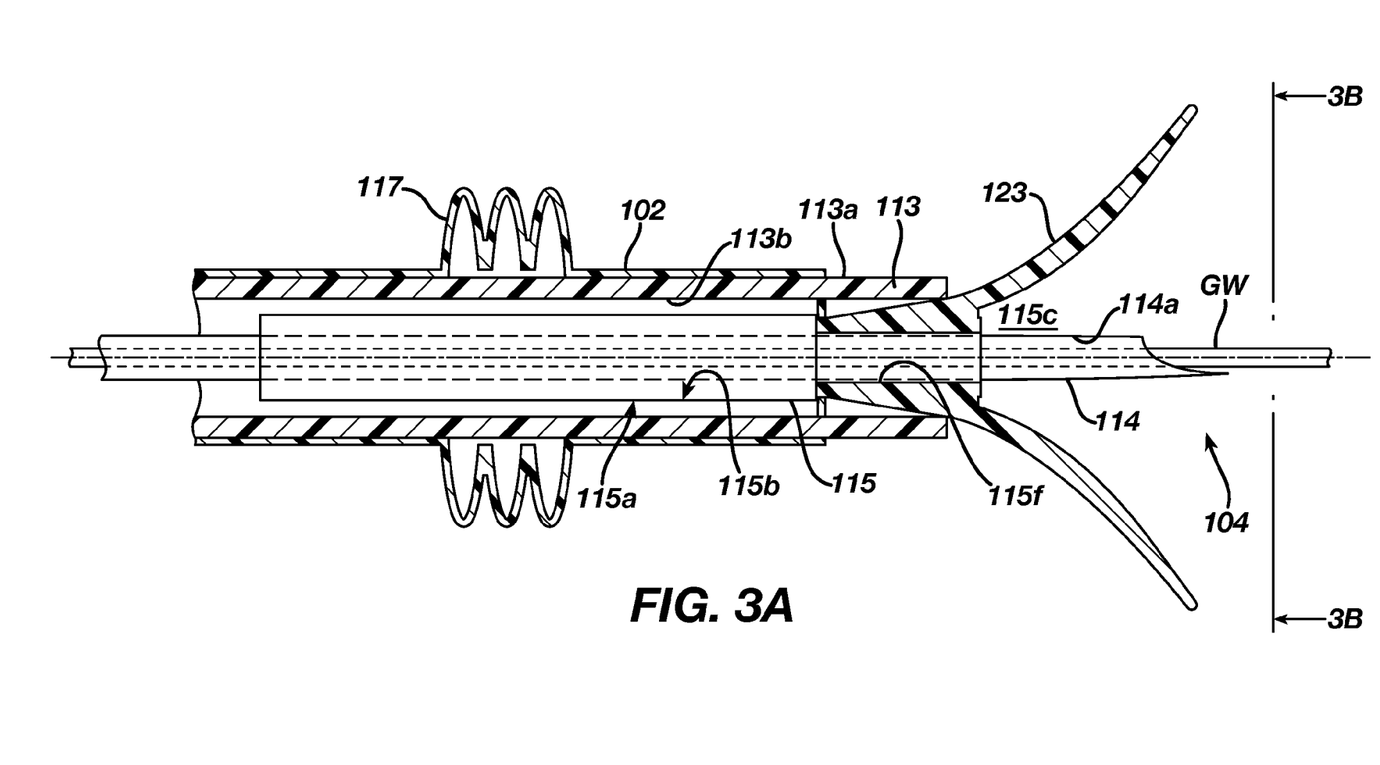
FIG. 3A illustrates (not to scale) a cross-sectional view of the distal end of the system in FIG. 2.
Figure 3B:
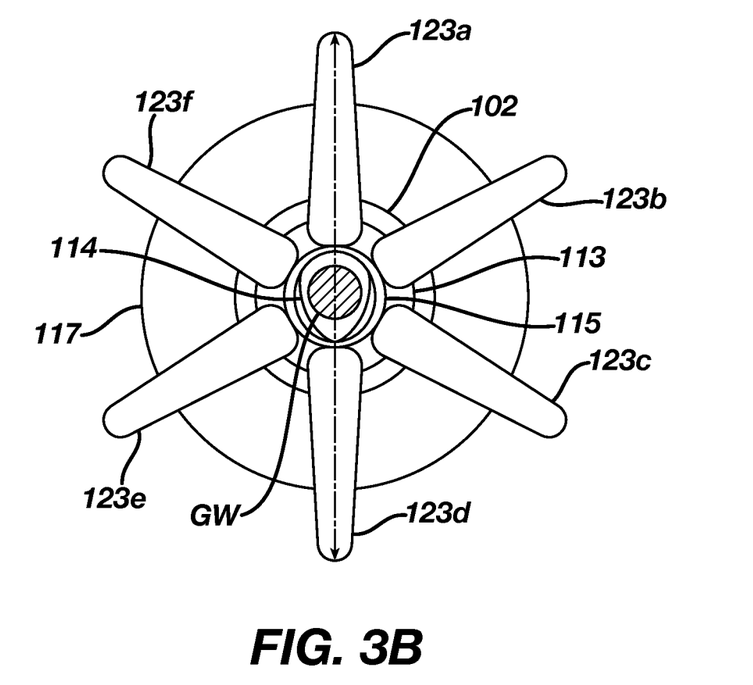
FIG. 3B illustrates, again not to scale, an end view of the distal end of the system in FIG. 3A.
Figure 4A:
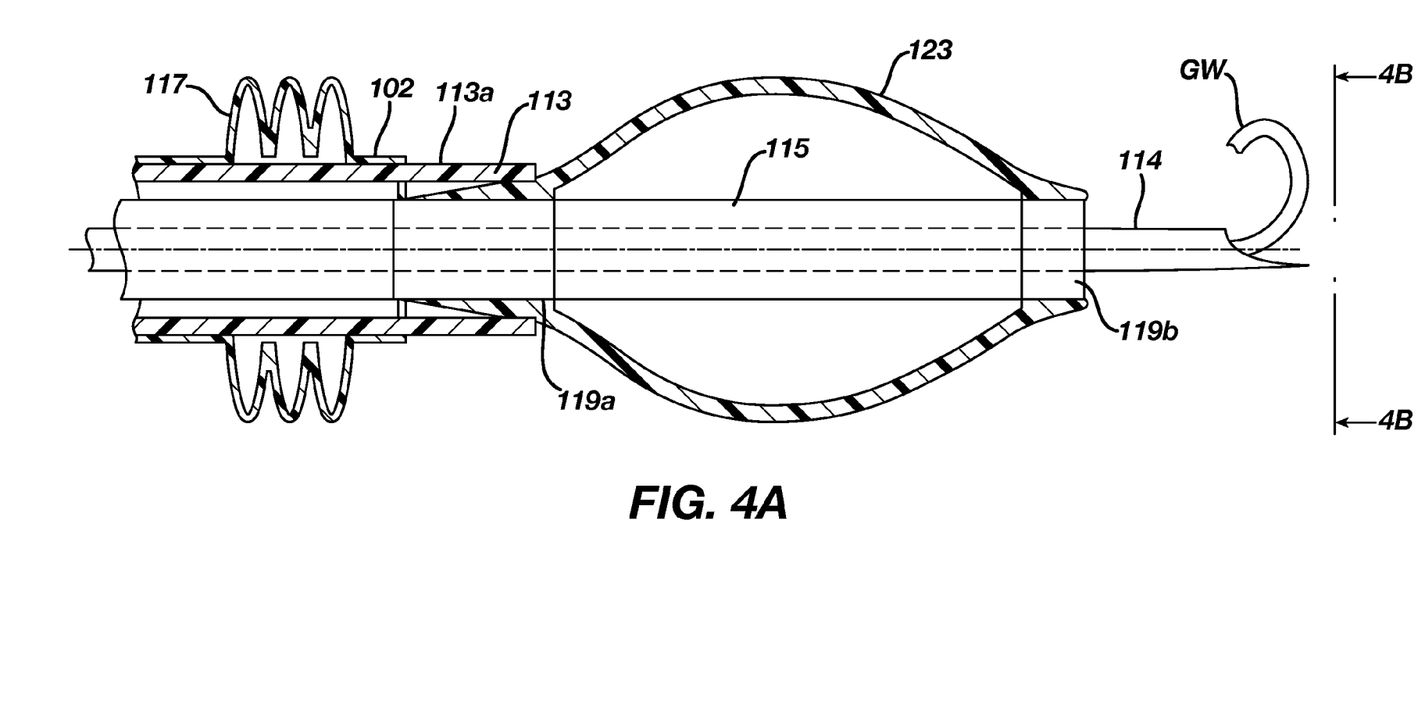
FIG. 4A illustrates (not to scale) a cross-sectional view of the distal end of the system in FIG. 2.
Figure 4B:
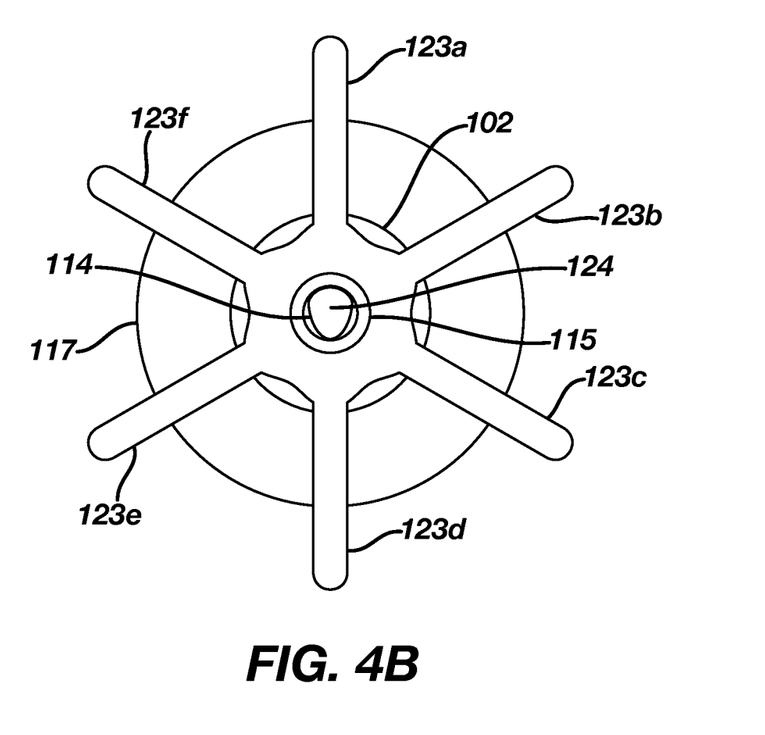
FIG. 4B illustrates, again not to scale, an end view of the distal end of the system in FIG. 4A.

Referring to FIG. 3A and moving from outside of catheter body 102 towards the longitudinal axis L-L, it can be seen that a plurality of concentric sheaths are provided in the catheter system 100. Specifically, a movable catheter sheath 113 is provided on the inside of the catheter body 102. The movable catheter sheath 113 has at least a portion surrounded by an internal surface 102a of the catheter body 102 and configured for movement along the longitudinal axis L-L with respect to the catheter body 102. It is noted that the movable catheter sheath 113 extends through the catheter handle 112 for manipulation by the operator. Continuing closer to the longitudinal axis is an inner catheter shaft 115 having a portion surrounded by an internal surface 113a of the movable catheter sheath 113. It is noted that the inner catheter shaft 115 has an expandable frame 123 attached proximate and end 113c of the inner catheter shaft 115. In one embodiment, shown in FIG. 3B, the expandable frame 123 may include six finger like projections disposed radially around the longitudinal axis L-L [clockwise] 123a, 123b, 123c, 123d, 123e, and 123f with each projection having a free end [as indicated by respective reference numerals] extending towards the distal end 104. In an alternative embodiment, shown here in FIGS. 4A and 4B, the expanding arms 123a-f are joined together at opposite ends via respective bosses 119a and 119b such that in the fully expanded configuration of FIGS. 4A and 4B, the arms take the configuration shown. Similar to the embodiment of FIG. 3A, the arms 123a-f may be self-expandable by virtue of a shape memory material, such as, for example, polymer or metal alloys including nitinol and variations thereof. It is noted here that in the unexpanded configuration for the arms (not shown for brevity) the expandable frames are constrained by the retractable sheath 113 such that the arms 123a-f are crimped to almost the same diameter as that of the inner sheath 115 and less than the inside diameter of the retractable sheath 113.

Referring back to FIGS. 3A and 3B, the cannula 114 has a portion surrounded by an internal surface 115b of the inner shaft 115. The outside surface 115a of the inner shaft 115 is surrounded by the inner surface 113b of the sheath 113. The cannula 114 is disposed for relative movement with respect to the inner shaft 115. Similar to the retractable sheath 113, the cannula 114 is configured to extend to and through the handle. The guidewire GW has a portion surrounded by an internal surface 114a of the cannula 114. As with other components, the guidewire GW is configured to extend through the cannula 114 to the handle 112 and extending outside the proximal end of the handle for manipulation by the operator. The sheaths 113 and 115 are formed from a suitable thermoplastic polymer or combinations of thermoplastic polymers.

Figure 4C:
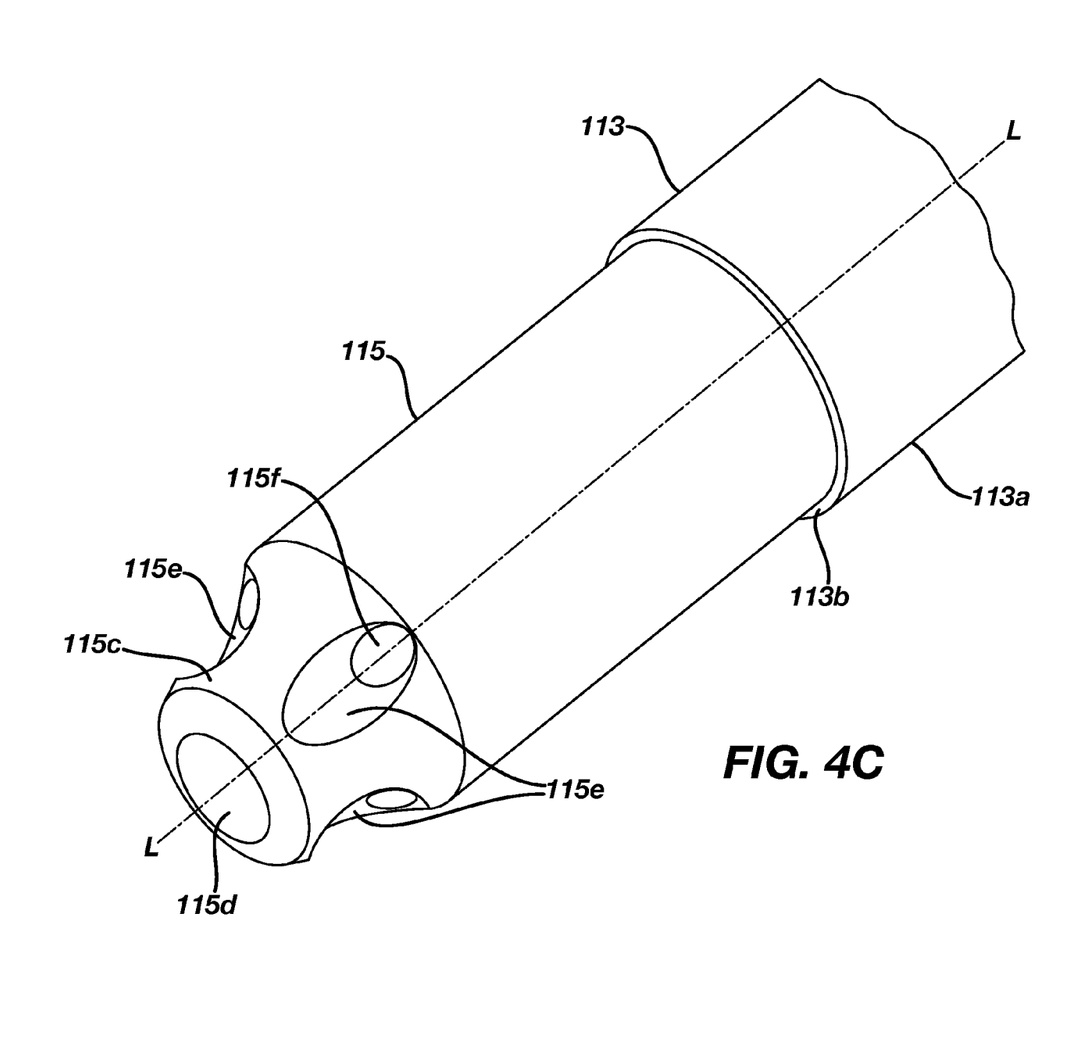
FIG. 4C illustrates a perspective view of the inner catheter shaft 115 in FIG. 3A or 4A.

Referring to FIG. 4C, certain other components are removed to show a better view of this portion of the inner catheter shaft 115 in a perspective. In this view, the inner catheter shaft 115 may have a terminal end portion 115c proximate the distal end 104 of the catheter 100 where a hollow tubular space is provided for movement of the cannula 114. In particular, the terminal end 115c has a plurality of slots 115e extending along the longitudinal axis L-L to allow the expandable arms 123a-f to extend through respective slots 115e from mounting boss 115f disposed inside the sheath 115. That is, the plurality of openings extends from the hub portion 115f through a generally conical surface of the terminal or second end 115c of the inner catheter sheath 115 to define generally elliptical through-slots 115e into the conical surface so that each of the expandable arms 123a-f extends from hub boss 115f therethrough the slots 115e. As shown here, the terminal end 115c of the sheath 115 is provided with the cannula opening 115d for movement of the cannula 114 relative to the inner sheath 115. Due to the nature of this device in the subintimal layer, all of the components can be configured so as to be symmetric with respect to the longitudinal axis L-L. This is unlike prior art devices in which the cannula, ports, and openings are asymmetric about the longitudinal axis.

By virtue of the systems and components described and illustrated herein, a method of crossing a chronic total occlusion in a blood vessel is provided. However, before discussing the details of the method, it is worthwhile to discuss the environment in which the method can be utilized such that a fuller understanding of the method can be gleaned by those skilled in the art and practiced with ease.

Figure 5:
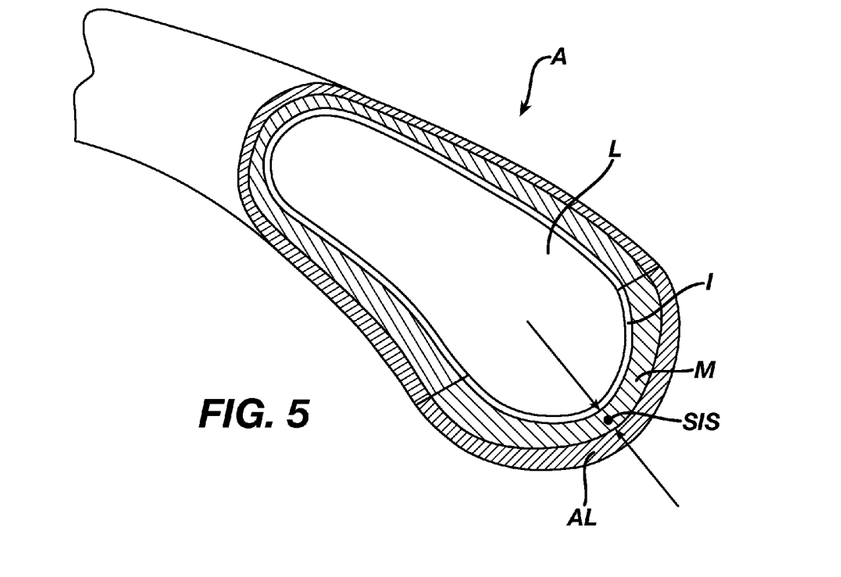
FIG. 5 illustrates a healthy blood vessel with a cross-sectional view of the various tissue layers.

As shown in FIG. 5, a normal (i.e., non-diseased) artery A is shown with a blood vessel lumen L and an arterial wall having a number of layers AL, M, SIS, and I. The innermost layer is referred to herein as the intimal layer I which includes the endothelium, the sub-endothelial layer, and the internal elastic lamina (not labeled). A medial layer M is concentrically outward from the intimal layer, and an adventitial layer AL is the outermost layer. Beyond the adventitial layer AL lies the extravascular tissue. As used hereinafter, the region between the intimal layer I and the adventitial layer AL, generally including the medial layer M, will be referred to as the subintimal space SIS. It is the subintimal space SIS through which the wires, deflecting catheters, and other catheter of the present invention will pass through the intimal layer I to return to the blood vessel lumen L of the artery A when crossing a total occlusion TO.

Figure 6:
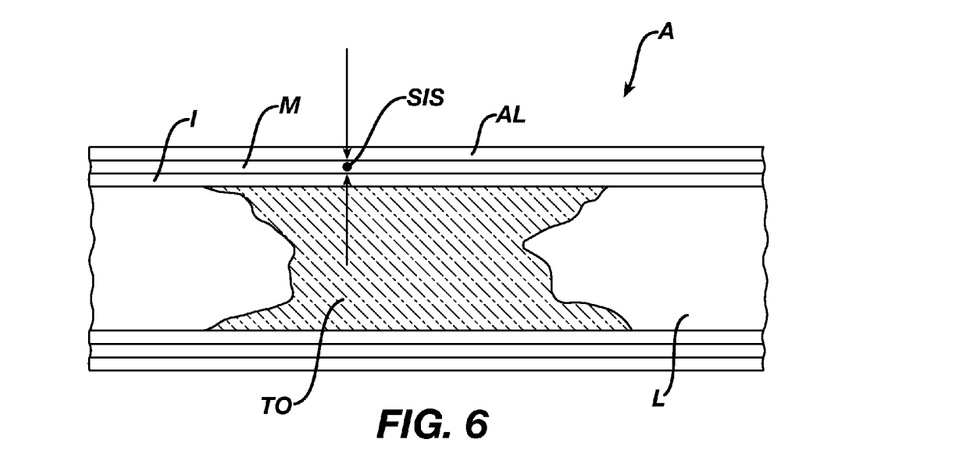
FIG. 6 illustrates a cross-sectional plan view of a diseased vessel having a total occlusion.
Figure 7A:
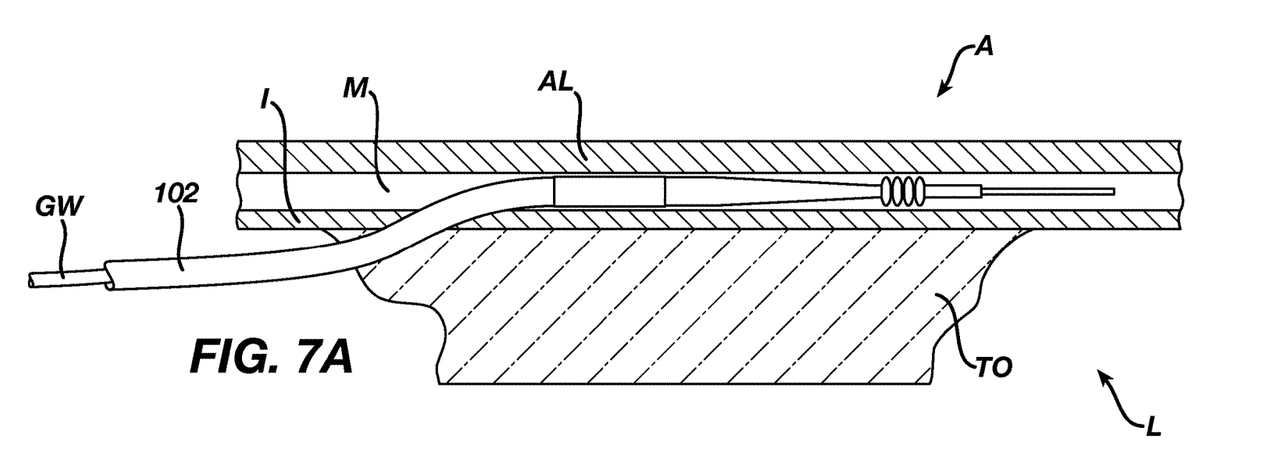
FIGS. 7A and 7B illustrate a sequence of steps performed during a re-entry procedure on a diseased artery.

In order to cross a total occlusion TO in FIG. 6, the method referred to earlier can be achieved by extending a catheter (described and illustrated earlier) into a space (e.g., subintimal space SIS) between an intimal layer I and an advential layer AL of the blood vessel before a chronic total occlusion TO. In FIG. 7A, it is assumed that this step has been achieved and the catheter body 102 is in the sub-intimal space SIS. Once inside, the catheter 102 is advanced until a terminal end of one of the cannula and guidewire is past the chronic total occlusion TO, shown here in FIG. 7A.

At this point in the method, the expandable frame 123 is expanded, either by retracting the sheath 113 to allow the frame 123 to self-expand. When expanded, the frame 123 impinges (via arms 123a-f) against the intimal layer I and the advential layer AL. Because the intimal layer I is thinner and structurally weaker than the advential layer AL, a bulge is formed on the inside surface of the blood vessel lumen L (i.e., a "tenting" effect) into the flow passage L of the blood vessel. Here, the stiffened section 111 with the articulation joint 117 and the tenting effect all work together to pivot the terminal portion 115d of the inner catheter sheath 115 at an angle towards the vessel lumen L in FIG. 7B.

Figure 7B:
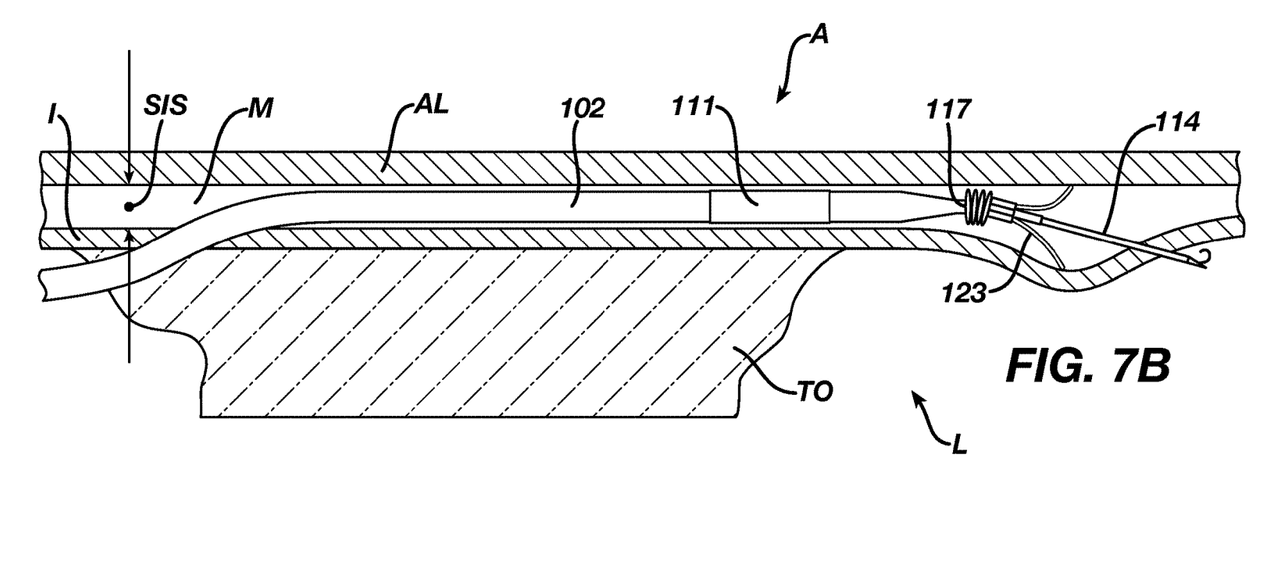

Thereafter, the operator can advance the cannula 114 to penetrate through the intimal layer I into the flow passage L of the blood vessel. Once the cannula 114 extends into the lumen L, the guidewire can be deployed in the blood vessel lumen L while the catheter body 102 (and related components) can be withdrawn proximally. This leaves the guide wire GW in place for introduction of other interventional catheters or deployment-type catheter devices. As can be seen, the advantage of our invention is that the cannula is symmetric (i.e., centered) with respect to the longitudinal axis such that there is one less requirement on the operator when preparing for re-entry around the occlusion. In other words, our invention does not require the operator to rotate the catheter body 102 or cannula 114 under fluoroscopy to ensure the correct orientation of the cannula as the correct orientation is obtained inherently by design of the system. Another advantage of our invention over the prior art is that there is no need to inflate and monitor inflation pressure to prevent bursting of any balloon inside the blood vessel.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:
1. A catheter system comprising:
   a catheter handle extending along a longitudinal axis from a first end to a second end, the handle having a hollow tubular portion extending through the handle, a fitting proximate the first end, a hemostatic fitting proximate the second end and a side port disposed between the first and second ends;
   a catheter body that extends from the catheter handle along the longitudinal axis from a proximal catheter end to a distal catheter end, the catheter body including an articulation joint interposed between portions of the catheter body proximate the distal end;
   a movable catheter sheath having a portion surrounded by an internal surface of the catheter body and configured for movement along the longitudinal axis with respect to the catheter body, the catheter sheath extending through the catheter handle;
   an inner catheter shaft having a portion surrounded by an internal surface of the movable catheter sheath, the inner catheter shaft having an expandable frame attached proximate one end of the inner catheter shaft, the expandable frame includes a plurality of self-expanding arms disposed radially about the longitudinal axis and each of the self-expanding arms includes a free end, the inner catheter shaft including a terminal end proximate the distal end of the catheter, the terminal end having a plurality of slots extending along the longitudinal axis to allow the expandable arms to extend through respective slots along the longitudinal axis, wherein the plurality of slots extend through a conical surface of the terminal end to define generally elliptical through-slots into the conical surface so that the free end of each of the expandable arms extends therethrough;
   a cannula having a portion surrounded by an internal surface of the inner shaft and disposed for movement with respect to the inner shaft, the cannula configured to extend to the handle; and
   a guidewire having a portion surrounded by an internal surface of the cannula, the guidewire configured to extend through the cannula to the handle.

2. The catheter system of claim 1, in which the catheter body includes a stiffened portion closer to the distal end than the proximal end, the stiffened portion being stiffer than the catheter body.

3. The catheter system of claim 1, in which the self-expanding arms comprise a nitinol material.

4. An endovascular catheter comprising:
   a catheter body that extends along the longitudinal axis from a proximal catheter end to a distal catheter end, the catheter body including an articulation joint interposed between portions of the catheter body proximate the distal end;
   an inner catheter shaft having a portion surrounded by an internal surface of the catheter body, the inner catheter shaft having an expandable frame attached proximate one end of the inner catheter shaft, the expendable frame includes a plurality of self-expanding arms disposed radially about the longitudinal axis and each of the self-expanding arms compromises a free end, the inner catheter shaft including a terminal end proximate the distal end of the catheter, the terminal end having a plurality of slots extending along the longitudinal axis to allow the respective free ends of the self-expanding arms of the expandable frame to extend through respective slots, wherein the plurality of slots extend through a conical surface of the terminal end to define generally elliptical through-slots into the conical surface so that the free end of each of the expandable arms extends therethrough; and a cannula having a portion surrounded by an internal surface of the inner shaft and disposed for movement with respect to the inner shaft, the cannula configured to extend through the inner catheter shaft.

5. The catheter of claim 4, in which the catheter body includes a stiffened portion closer to the distal end than the proximal end, the stiffened portion being stiffer than the catheter body.

6. The catheter of claim 4, in which the self-expanding arms comprise a nitinol material.

* * * * *